United States Patent [19]

Botta

[11] 3,936,444
[45] Feb. 3, 1976

[54] PRODUCTION OF ARYL LACTAM-HYDRAZONES

[75] Inventor: Arthur Botta, Krefeld, Germany

[73] Assignee: Bayer Aktiengesellschaft, Leverkusen, Germany

[22] Filed: July 9, 1973

[21] Appl. No.: 377,862

[30] Foreign Application Priority Data
July 18, 1972 Germany............................ 2235177

[52] U.S. Cl. ...... 260/239 B; 260/239 A; 260/239 E; 260/239 BE; 260/293.69; 260/293.79; 260/296 R; 260/288 CE; 260/305; 260/309.2; 260/326.86; 260/326.5 L; 260/326.9; 424/244; 424/263; 424/270; 424/273; 424/274
[51] Int. Cl.² .............. C07D 223/12; C07D 213/77; C07D 207/14; C07D 211/56
[58] Field of Search..... 260/239 B, 239 BE, 326.86, 260/293.79, 296 R, 293.69, 326.5 L

[56] References Cited
FOREIGN PATENTS OR APPLICATIONS
1,957,783   5/1971   Germany....................... 260/239 F OTHER PUBLICATIONS
P. Cefelin et al., Coll. Czech. Chem. Comm. 25, 2522 (1960).
A. Le Berre et al., Bulletin de La Soc. Chim. de France, 1971, 3245.

Primary Examiner—R. Gallagher
Assistant Examiner—Mark L. Berch
Attorney, Agent, or Firm—Burgess, Dinklage & Sprung

[57] ABSTRACT

In the production of an aryl lactamhydrazone of the formula

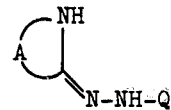

(I)

in which
A represents optionally substituted alkylene, aralkylene or cycloalkylene, each with up to 20 carbon atoms, and
Q represents optionally substituted, mononuclear to trinuclear aryl or an optionally alkylsubstituted mononuclear or binuclear heterocyclic aromatic system with 1 to 3 hetero atoms,
in which a lactim-ether of the formula

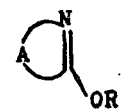

(II), in which R is aryl or alkyl of 1 to 6 carbon atoms,
is reacted with an arylhydrazine or heteroarylhydrazine of the formula
$H_2N-NH-Q$   (III)
the improvement which comprises effecting the reaction at a temperature of about −20° to 150°C and in the presence of at least a catalytic amount of acid, whereby the yield is markedly increased. Those compounds wherein A is $-(CH_2)_{2-11}-$ and Q is pyridyl or phenyl substituted by at least one nitro, sulfo, sulfonamido or carboxy group are new and exhibit fungicidal activity.

3 Claims, No Drawings

PRODUCTION OF ARYL LACTAM-HYDRAZONES

The present invention relates to an unobvious process for the production of certain fungicidal aryl lactam-hydrazones of aromatic systems and their acid addition salts, and to some of these compounds which are new.

It is known to produce the phenylhydrazones of caprolactam and of pyrrolidone by reaction of phenylhydrazine with the appropriate lactim-methyl-ethers at temperatures around 80° to 200°C. However, in the course thereof severe decomposition with formation of ammonia occurs and the yield of the lactam-phenylhydrazones, which are unstable and oxidation-sensitive compounds, is moderate (see, on this subject, Chem. Abstr. 54, 24,712 c and Bull. Soc. Chim. France 1969 (10), 3,704–12). Arylhydrazines substituted by electronegative radicals, such as nitro groups, cannot be reacted at all in this way with lactim-alkyl-ethers. Furthermore, substituted arylhydrazones of pyrrolidone, piperidone and caprolactam have been prepared, in an analogous manner, by reaction of substituted arylhydrazines with the corresponding lactim-methyl-thioethers or lactimchlorides (see German Offenlegungsschrift (German Published Specification) 1,957,783). The yields of 11.7% or 32.5% of theory thereby achieved can hardly serve as the basis of an industrially economical process. The use of lactim-methyl-thioether also yields, as a by-product, the toxic and evil-smelling methylmercaptan, which makes the conduct of the reaction, and working up, more difficult.

The present invention provides a process for the production of a lactam-hydrazone of an aromatic system, of the general formula

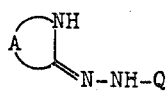
(I)

in which
A is optionally substituted alkylene, arylalkylene or cycloalkylene, each of up to 20 carbon atoms, and
Q is optionally substituted mononuclear, dinuclear or trinuclear aryl or optionally alkyl-substituted mononuclear or binuclear heterocyclic aryl having 1 to 3 hetero-atoms, or an acid-addition salt thereof, in which a lactim-ether of the general formula

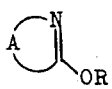
(II)

in which
A has the above-mentioned meaning, and
R is $C_1$–$C_6$ alkyl or aryl, is reacted, in the presence of at least a catalytic amount of an acid and at a temperature between about −20° and +150°C, with an arylhydrazine or heteroarylhydrazine of the general formula $$H_2N-NH-Q \qquad (III)$$

in which
Q has the above-mentioned meaning.

Preferably A is an alkylene group $-(CH_2)_n-$, wherein $n$ is an integer from 2 to 11, the alkylene group being optionally substituted by at least one of $C_1$–$C_6$ alkyl and pheny; R represents methyl, ethyl or phenyl; and Q is (a) phenyl optionally carrying at least one substitutent selected from the group consisting of $C_1$–$C_6$ alkyl, fluorine, chlorine, bromine, nitro, methoxy, methylthio, methylsulfonyl, di-($C_1$–$C_6$ alkyl)amino, amidosulfonyl, amidocarbonyl, sulfo and carboxy, (b) naphthyl, chloronaphthyl or methoxynaphthyl, or (c)

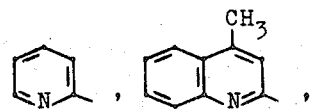

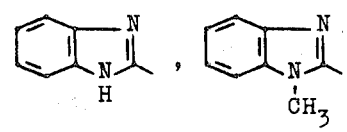

or 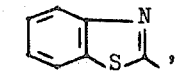

optionally substituted by at least one $C_1$–$C_6$ alkyl, fluorine, chlorine, bromine, methoxy or nitro group.

It is extremely surprising that merely catalytic amounts of an acid cause an enormous acceleration of the reaction velocity, a lowering of the reaction temperature and a considerable rise in the yield.

Compared with the prior-art processes, the process according to the invention provides substantially higher yields and renders obtainable even those lactamarylhydrazones which could not previously be produced, for example nitroarylhydrazones. Furthermore, the process conditions do not require an increase expenditure of energy, since the reaction temperatures in most cases produce a sufficiently rapid course of the reaction even near room temperature. As a result of the mild and gentle reaction conditions, sensitive starting materials can also be employed and the above-mentioned decomposition phenomena, which lead to considerable losses in yield in the customary processes, remain entirely absent. A further advantage of the process according to the invention is that it can, if desired, furnish directly, in a single process stage, the acid-addition salts, which as a rule are the forms used for biological preparations. These acid-addition salts are in most cases substantially more stable compounds than the free lactamarylhydrazones (I) or (I), which are sensitive to oxidation by air, and they crystallize better, so that their working up and purification is considerably simplified.

The compounds prepared according to the invention are present in the following tautomeric equilibrium:

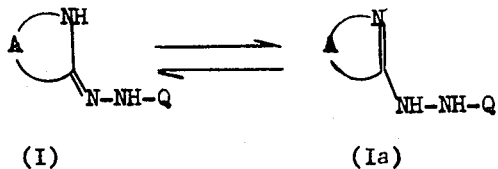

For reasons of simplicity, the formula I and species thereunder are intended, in each individual case, also to encompass the corresponding tautomeric formula (Ia).

If, for example, caprolactim-methyl-ether and 3-chlorophenylhydrazine in the presence of hydrogen chloride are used as starting materials in the process according to the invention, the course of the reaction can be represented by the following equation:

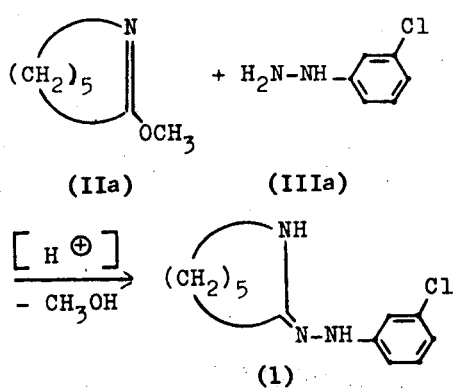

The lactim-ethers required as starting materials are defined generally by the formula (II).

As examples of lactams which are suitable for the process and on which the lactim-ethers (II) are based, there may be mentioned: 3-propiolactam, 3-phenyl-, 3-vinyl-, 3,3-diphenyl-, 2,3-diphenyl, 3-methyl-, 3-ethyl-, 3-benzyl-, 3,3-dimethyl- and 2,3,3-trimethyl-propiolactam, 4-butyrolactam, 4,4-dimethyl-butyrolactam, 5-valerolactam, 2,5-ethylenevalerolactam, 6-caprolactam, 4-tert.-butyl-6-caprolactam, 2-nitro-6-caprolactam, the 2-to 6-methylcaprolactams, the 2-to.6-phenylcaprolactams, 7-oenantholactam, 8-capryllactam, 12-lauroyllactam, naphthostyril, phenanthridone, phthalimidine, hexahydro-phthalimidine, morpholone, benzmorpholone, octahydroquinolone-2, 1H-4-methyl-hexahydro-1,4-diazepin-2-one, 1H-4-cyclohexyl-hecahydro-1,4-diazepin-2-one, 1H-2-oxo-5-ethyl-1,5-diazacyclooctane and 2-oxo-5,6-benztetrahydroazepine. The methyl-, ethyl- or phenyl-ethers are preferred as lactim-ethers for the process according to the invention. The manufacture of the lactim-ethers is known (see Houben-Weyl, "Methoden der organisc-hen Chemie"("Methods of Organic Chemistry"), volume 11/2, page 578; also German Offenlegungsschrift (German Published Specifications) 1,912,739 and 1,912,737; further J. Amer.chem.Soc.70, 2116(1948)).

The arylhydrazines and heteroarylhydrazines which are also required as starting materials are defined generally by the formula (III).

Examples of suitable arylhydrazines according to the formula (III) are phenylhydrazine, the o-, m- and p-isomers of tolyhydrazine, tert.-butylphenylhydrazine, fluoro-, chloro-, bromo-, iodo-, nitro-, methoxy-, ethoxy-, methylmercapto-, dimethylamino-, trifluoromethyl- and methylsulfonyl-phenylhydrazines, hydrazinobenzoic acid amide, hydrazinobenzenesulfonamide, hydrazinobenzoic acid and hydrazineosulfonic acid, 2,6-dimethyl-, 2-chloro-6-methyl-, 4-chloro-2-methyl-, 2,6-dichloro-, 3,4-dichloro-, 3,5-dichloro-, 2,4-dichloro-, 2,4,6-trichloro-, 2,4-dinitro-, 3,5-dinitro-, 4-chloro-2-nitro-, 2-chloro-3-nitro-, 2-nitro4-methyl- and 2-chloro-5-sulfo-phenylhydrazines, 1- and 2-hydrazinonaphthalenes, hydrazinoanthracene and hydrazinophenanthrene.

Examples of suitable heteroarylhydrazines according to the formula (III) are 2-, 3- and 4-hydrazino-pyridines, 2- hydrazino-4-methyl-pyridine, 4-hydrazino-2,6-lutidine, 2-, 3-and 4-hydrazinoquinolines, 2-hydrazino-4-methyl-quinoline, 2-hydrazino-pyrimidine, 2-hydrazino-s-triazine, 3-hydrazino-1, 2,4-triazine, 3-hydrazino-1-methyl-pyrazole, 2-hydrazinoimidazole, 2-hydrazino-1-phenyl-imidazole, 2-hydrazino-4,5-dimethyl-imidazole, 2-hydrazino-benzimidazole, 5-hydrazinobenzimidazole, 5-chloro-, 5-methyl-, 5-methoxy-, 5-nitro-, 5-dimethylamino-1-methyl-, 1-benzyl- and 1-phenyl-2-hydrazino-benzimidazoles, 2-hydrazino-thiazole, 2-hydrazino-4-methyl-thiazole, 3-hydrazino-isoxazole, 5-hydrazinobenzoxazole and 2-hydrazino-, 5-bromo-2-hydrazino- and 5-nitro-2-hydrazino-benzthiazoles.

The arylhydrazines and heteroarylhydrazines of the formula (III) may be prepared according to generally known processes. Preparative instructions are to be found, for example, in Houben-Weyl "Methoden der organischen Chemie", ("Methods of Organic Chemistry"), volume 10/2, the section on "Nitrogen I/2", page 169 and thereafter.

Though the reaction according to the invention can be carried out without diluents, it is advantageous to use, in particular, polar solvents, for example water; alcohols, such as methanol, ethanol, propanol, isopropanol, butanol, hexanol, cyclohexanol, glycol, glycerine, O-methylgycol, O-butylglycol, dihydroxydiethyl ether and triethanolamine; phenols, such as phenol, cresol, chlorophenol, dichlorophenol and hydroxybenzoic acid ethyl ester; carboxylic acids, such as formic acid, acetic acid, propionic acid, lactic acid, dichloroacetic acid and trifluoroacetic acid; acid amides, such as dimethylformamide and N-methylpyrrolidone; nitrohydrocarbons, such as nitromethane and nitrobenzene; ethers, such as tetrahydrofurane and dioxane; dimethylsulfoxide; or mixtures of these solvents.

According to the invention, the reaction is carried out in the presence of an acid as a reaction accelerator. Acids which can be used for the process according to the invention are, for example, hydrochloric acid, hydrobromic acid, hydroiodic acid, dilute perchloric acid, tetrafluoroboric acid, dilute nitric acid, sulfuric acid, potassium bisulfate, monomethylsulfuric acid, monoethylsulfuric acid, methanesulfonic acid, benzene sulfonic acid, toluenesulfonic acid, phosphoric acid, cyclohexylphosphonic acid, phenylphosphonic acid, formic acid, acetic acid, dichloroacetic acid, trifluoroacetic acid, propionic acid, caproic acid, oxalic acid, fumaric acid, maleic acid, lactic acid, malic acid, tartaric acid, citric acid, benzoic acid, p-chlorobenzoic acid, p-hydroxybenzoic acid, p-nitrobenzoic acid, phenylacetic acid, cinnamic acid, phthalic acid, isophthalic acid, terephthalic acid, phenol, chlorophenol, nitrophenol, 2,4-dinitrophenol and picric acid, Furthermore, Lewis acids which can form complex proton-acids of the type $H^+[MCl_xOR]^-$ with the solvent can also be used for the process according to the invention and, moreover, such complex acids can also be employed directly; examples are aluminum chloride, iron-(III)chloride, boron fluoride, tin(II)chloride, tin(IV)-chloride, titanium(IV) chloride and antimony pentachloride. Commercially available inorganic or organic acid ion exchangers or molecular sieves can also be used with advantage for the process according to the invention.

The reaction temperature can be varied over a fairly wide range and it depends on the reactivity of the lactim-ether employed which, for example, is a function of the ring size, on the reactivity of the (hetero)arylhydrazine used and on the nature and amount of the acid catlyst. In general, the temperature is between $-20°C$ and $+150°C$, and in most cases between $-10°$ and $+100°C$.

Depending on which is the more readily obtainable, it is possible to employ either the lactim-ether component or the (hetero)arylhydrazine component in excess, for example up to 0.5 mole. Usually, however, the lactim-ether and the (hetero)arylhydrazine are reacted with each other in a molar ratio of about 1:1.

The amounts of acid catalyst which are required for the process according to the invention can be varied and depend firstly on the reactivity of the lactim-ethers employed and on the basicity of the (hetero)arylhydrazines used, and additionally on which end product of the process is desired. If it is desired to obtain the free lactamarylhydrzone (I), about 0.1 to 50 mole% preferably 1 to 10 mole%, of acid catalyst in general sufficies; if the acid-addition salt is required, the desired acid is as a rule employed in about stoichiometric molar ratio with respect to the lactim-ether or (hetero)arylhydrazine, i.e. 1:1 in most instances. Larger amounts of acid are not essential but can at times be of advantage, for example in cases where the acid — for example carboxylic acids or phenols — can at the same time be used as a solvent for the reaction.

The usual embodiment of the process accoording to the invention is initially to take the lactim-ether and (hetero)arylhydrazine, optionally dissolved or suspended in a suitable solvent, to add the acid catalyst and to bring the reaction mixture to the reaction temperature. It is, however, also possible first to take the hydrazine and the acid catalyst or the hydrazine acid-addition salt and to add the lactim-ether, or, conversely, to take first the lactim-ether, optionally together with acid, and to introduce the hydrazine or hydrazine salt into the reaction mixture.

An embodiment of the process according to the invention which is particularly advantageous because it is economical consists of preparing the lactim-ethers in the form of their acid-addition salts in a known manner (see Houben-Weyl, "Methoden der organischen Chemie" ("Methods of Organic Chemistry"), volume 11/2, page 578 and German Offenlegungsschriften (German Published Specifications) 1,912,737 and 1,912,739) by alkylation or acylation of lactams and to react these acid-addition salts as such directly and without intermediate isolation of the free lactim-ethers, but optionally with the addition of a suitable solvent or diluent, with the (hetero)arylhydrazines.

The reaction products are worked up in the usual manner. If the products of the process are directly obtained as acid-addition salts, they can be isolated as such and be purified by recrytallization. In cases where it is desired to obtain the products of the process in the form of the free lactam (hetero)arylhydrazones (I), the reaction mixture is appropriately extracted, before further working up, with aqueous alkalis, for example a solution of sodium hydroxide, potassium hydroxide, sodium carbonate, sodium bicarbonate or potassium bicarbonate, while optionally using suitable solvents which are immiscible with water or of only limited miscibility therewith; thereafter the free lactam(-hetero)arylhydrazones are isolated and purified by distillation and/or recrystallization or are optionally converted into the desired acid-addition salt by adding the corresponding acid.

The process products of the formula (I) and their acid-addition salts are valuable fungicides as described in Application Ser. No. 377,861, filed July 9, 1973, now pending.

Some of the lactamhydrazones of aromatic systems, which can be prepared according to the present invention, have already been described in the literature (see, on this matter, Chem. Abstracts 54, 24,712 c; Bull. Soc. Chim. France 1969 (10), 3,704–3,712; and German Offenlegungsschrift (German Published Specification) 1,957,783). The other compounds of formula (I) have not hitherto been described. Interesting new compounds with fungicidal properties against fungi that damage plants are, for example, those of the formula (I) in which A is an alkylene grouping $—(CH_2)_n—$, n is an integer from 2 to 11, and Q is a pyridyl radical, or a phenyl radical carrying at least one nitro, sulfo, sulfonamido or carboxyl group, and their acid-addition salts.

The invention is illustrated in the following Examples:

EXAMPLE 1a

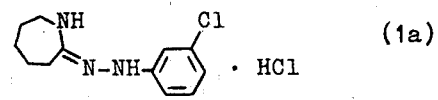

300 G of hydrogen chloride gas were introduced into a solution of 1,000g (7 moles) of 3-chlorophenylhydrazine and 980 g (7.7 moles) of caprolactim-methyl-ether in 4,000 ml of methanol at 10° to 20°C while stirring and cooling with an ice bath, and the reaction mixture was kept for a further hour at 20°C, raised to the reflux temperature and kept at 65°C for 1½ hours. After cooling, the crystals which had separated out were filtered off and further crystal fractions were isolated by concentrating the mother liquors under reduced pressure. After recrystallization from 2 parts of methanol, 1,845 g (96% of theory) of caprolactam-(3-chlorophenylhy-

EXAMPLE 1b

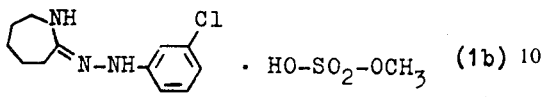

56.6 G (0.5 mole) of caprolactam were fused and 63.1 g (0.5 mole) of dimethyl sulfate were allowed to run into the melt at 70° to 80°C. The mixture was kept at 80° to 90°C for a further 2 hours and cooled, and the viscous melt was taken up in 250 ml of methanol. Reaction with 72 g (0.5 mole) of 3-chlorophenylhydrazine was then carried out in the same manner as indicated in Example 1a, and 99.5 g (57% of theory) of caprolactam-(3-chlorophenylhydrazone) monomethylsulfate were obtained as colorless crystals of melting point 135°C. On concentrating the mother liquors and treating with excess sodium hydroxide solution, 33.3 g (28% of theory) of caprolactam-(3-chlorophenylhydrazone) of boiling point 180°C/0.08 mmHg were obtained. The total yield was 85% of theory.

EXAMPLE 1c

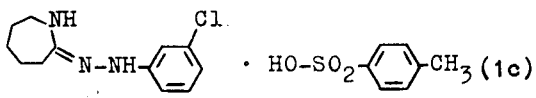

A mixture of 56.6 g (0.5 mole) of caprolactam and 93 g (0.5 mole) of p-toluenesulfonic acid methyl ester was fused and kept at 90°C for 3 hours. Thereafter the melt was cooled and taken up in 250 ml of methanol. The further reaction with 72 g (0.5 mole) of 3-chlorophenylhydrazine took place analogously to Example 1a. The yield of caprolactam-(3-chlorophenylhydrazone)-p-toluenesulfonate was 104.5 g (51% of theory) as colorless crystals of melting point 220°C.

The mother liquor yielded, analogously to Example 1b, 25 g (21% of theory) of caprolactam-(3-chlorophenylhydrazone). The total yield was 72% of theory.

EXAMPLE 1d

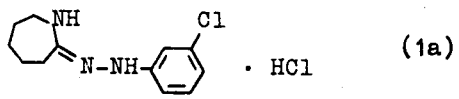

35 G (0.28 mole) of caprolactim-methyl-ether were added dropwise over the course of 15 minutes at 0° to 5°C, while stirring well, to a suspension of 45 g (0.25 mole) of 3-chlorophenylhydrazine hydrochloride in 500 ml of water; the temperature was then allowed to rise to 20°C over the course of 1½ hours and the mixture was kept at this temperature for a further 1½ hours. Thereafter it was filtered off and yet further crystal fractions were isolated by concentrating the mother liquor under reduced pressure. After drying, the yield of caprolactam-(3-chlorophenylhydrazone) hydrochloride was 65 g (94.7% of the theory).

EXAMPLE 1e

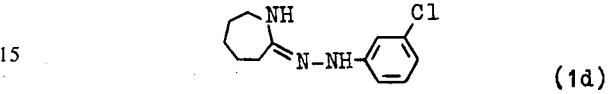

35 G (0.28 mole) of caprolactim-methyl-ether were added dropwise over the course of 15 minutes at 5°C, while stirring and cooling, to a solution of 36 g (0.25 mole) of 3-chlorophenylhydrazine in 250 ml of glacial acetic acid; the red-brown clear solution was kept at 0° to 5°C for a further 2 hours and then for 2 hours at 20°C and excess glacial acetic acid was distilled off in a water-pump vacuum. On fractional distillation in vacuo of the residue which remained, 56 g (94.3% of theory) of caprolactam-(3-chlorophenylhydrazone) were obtained; it was a light viscous oil of boiling point 215° to 220°C/3 mmHg, which solidified to crystals.

EXAMPLE 1f

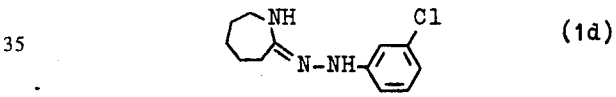

35 G (0.28 mole) of caprolactim-methyl-ether were run into a solution of 36 g (0.25 mole) of m-chlorophenylhydrazine in 300 ml of o-chlorophenol at 0°C, while stirring and cooling; the temperature was allowed to rise to 20°C and the mixture was then additionally heated to 80°C for 1½ hours. On fractional distillation in vacuo, a first runnings of o-chlorophenol was followed by 55 g (92.7% of theory) of caprolactam-(m-chlorophenylhydrazone) of boiling point 180° to 184°C/0.08 mmHg.

EXAMPLE 2

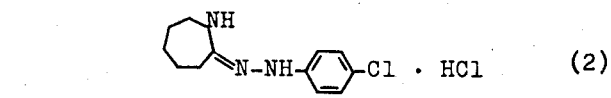

When, analogously to Example 1a, the same amount of 4-chlorophenylhydrazine was employed instead of 3-chlorophenylhydrazine, 1,750 g (91% of theory) of carpolactam-(4-chlorophenylhydrazone) hydrochloride were obtained as colorless crystals of melting point 260°C (with decomposition).

EXAMPLE 3

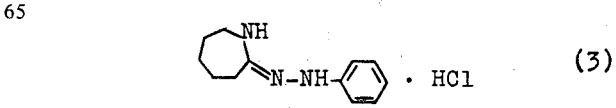

127 G (1 mole) of caprolactim-methyl-ether were added dropwise over the course of 30 minutes to a mixture of 144.5 g (1 mole) of phenylhydrazine hydrochloride and 700 ml of anhydrous ethanol at −10°C, while stirring well and cooling; the mixture was kept for a further hour at −10°C, then for 2 hours at room temperature and for 30 minutes at the reflux temperature. After cooling, the mixture was filtered and further crystal fractions were isolated by concentrating the mother liquor under reduced pressure. Recrystallization from 5 parts of ethanol yielded 220 g (92% of theory) of caprolactam-phenylhydrazone hydrochloride as almost colorless crystals of melting point 244° to 246°C (with decomposition).

COMPARISON EXAMPLE 3a (Preparation of the free base of the compound described in Example 3, in accordance with a prior-art process.)

When a mixture of 127 g (1 mole) of caprolactim-methylether and 108 g (1 mole) of phenylhydrazine was heated from 140° to 200°C over the course of 6 hours, 34 g (theoretically 32 g of methanol) of a distillate with a pungent smell of ammonia passed over at boiling point 60° to 140°C. The distillation of the reaction product yielded, in addition to a first runnings of starting material and 35 g of distillation residue, 92 g of caprolactam-phenylhydrazone of boiling point 125°C/0.1 mm Hg, in the form of a yellow crystalline mass which assumed a resinous brown discoloration in air. The yield was only 45.5% of theory.

EXAMPLE 4

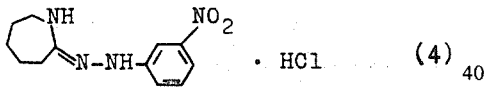   . HCl   (4)

210 G (1.65 moles) of caprolactim-methyl-ether were run into a suspension of 285 g (1.5 moles) of 3-nitrophenylhydrazine hydrochloride in 3,500 ml of methanol at 20°C while stirring well and cooling, whereupon solution first occurred and thereafter a precipitate was again formed gradually. The mixture was then warmed to the reflux temperature and kept at 65°C for a further 2 hours. After cooling, the product was filtered off and the crystals were washed with a large amount of water and recrystallized from 15 parts of methanol. The yield of caprolactam-(3-nitrophenylhydrazone) hydrochloride was 374 g (87.5% of theory) as yellow crystals of melting point 280°C (with decomposition).

COMPARISON EXAMPLE 4a

When, in accordance with the prior-art procedure, equimolar amounts of caprolactim-phenyl-ether and 3-nitrophenylhydrazine were employed for the preparation of the free base of the compound described in Example 4, and the mixture was gradually heated to 150°C under nitrogen without addition of a catalyst, an exothermic reaction took place. After stripping off the phenol under reduced pressure, a black resin remained, which could not be purified by distillation or by recrystalliztion.

EXAMPLE 5a

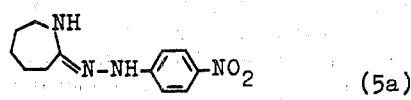   (5a)

A solution of 153 g (1 mole) of 4-nitrophenylhydrazine, 127 g (1 mole) of caprolactim-methyl-ether and 30 g (0.175 mole) of p-toluenesulfonic acid in 1,200 ml of anhydrous ethanol was kept, while stirring, for one hour at room temperature and then for 3 hours at the reflux temperature. Thereafter, the solvent was distilled off, initially under normal pressure and finally in a water-pump vacuum, the residue was taken up in 1,500 ml of 2% strength sodium carbonate solution and the precipitate was filtered off and recrystallized from 5 parts of methanol. The yield of caprolactam-(4-nitrophenylhydrazone) of melting point 190°C was 201 g (81% of theory).

EXAMPLE 5b

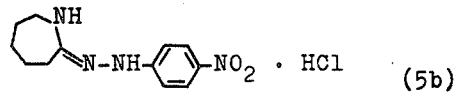   (5b)

When, instead of toluenesulfonic acid, 37 g (1 mole) of hydrogen chloride gas was used under the same reaction conditions, caprolactam-(4-nitrophenylhydrazone) hydrochloride was obtained in the form of yellow crystals of melting point 290°C (with decomposition).

EXAMPLE 6

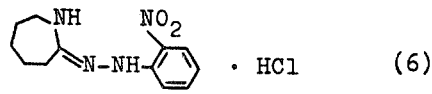   (6)

254 G (2 moles) of caprolactim-methyl-ether were allowed to run into a suspension of 404 g (2 moles) of 2-nitrophenylhydrazine sulfate in 2,000 ml of methanol while stirring and cooling at 20°C; the mixture was kept at room temperature for a further one-half hour and the solvent was distilled off, initially under normal pressure and finally in a water-pump vacuum. The residue which remained was dissolved in 2,000 ml of water, the solution was filtered and caprolactam-(2-nitrophenylhydrazone) was precipitated from the filtrate by means of an aqueous solution of 300 g of potassium carbonate. The red-brown crystals were filtered off, washed with copious amounts of water and dried in vacuo at 50°C. The product was sufficiently pure (melting point 158°C) but could be recrystallized from 6 parts of ethyl acetate, whereby red-brown crystals with a green gloss, of melting point 158° to 159°C, were obtained. The yield was 480 g (96% of theory). The hydrochloride of caprolactam-(2-nitrophenylhydrazone), which was easily obtainable by treating a solution of ethanol with the equivalent amount of concentrated hydrochloric acid, melts with decomposition, at 226°C; the salt is in the form of yellow crystals.

EXAMPLE 7

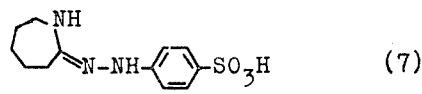   (7)

A solution of 64 g (0.5 mole) of caprolactim-methylether in 100 ml of ethanol was allowed to run into a mixture of 94 g (0.5 mole) of 4-hydrazinobenzene sulfonic and 700 ml of anhydrous ethanol at 20°C, while stirring, and the reaction mixture was brought to the refluxing temperature over the course of 2 hours and additionally kept for 5 hours at 80°C. After cooling, the product was filtered off and recrystallized from 20 parts of water to give colorless to grey crystals, which did not melt below 360°C (since an internal salt was present), of caprolactam(4-sulfophenylhydrazone); the yield was 116 g (82% of theory).

EXAMPLE 8

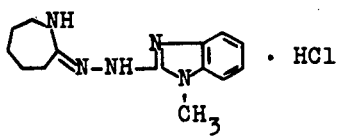

(8)

A solution of 55 g of concentrated hydrochloric acid in 260 ml of methanol was first allowed to run into a solution of 81 g (0.5 mole) of 2-hydrazino-1-methyl-benzimidazole in 500 ml of methanol, while stirring and cooling at 0°C, and thereafter a solution of 70 g (0.55 mole) of caprolactim-methyl-ether in 250 ml of methanol was added dropwise over the course of 30 minutes. The mixture was additionally kept for 2 hours at room temperature while stirring, and then for 3 hours at the reflux temperature, a little undissolved product was filtered off hot, the filtrate was cooled and the crystals were then filtered off. On concentrating the mother liquor under reduced pressure further crystal fractions were obtained. The total yield of caprolactam-[1-methyl-benzimidazolyl-(2)-hydrazone] hydrochloride was 135 g of colorless crystals of melting point 248° to 250°C, representing 92% of theory.

The following compounds were also prepared in a similar manner:

Table 1

| Compound No. | Formula | Physical properties |
|---|---|---|
| (9) | caprolactam-(2-nitrophenyl)hydrazone | Melting point 196°C monohydrochloride: melting point 256 to 258°C (with decomposition) |
| (10) | cyclotridecanone-(2-nitrophenyl)hydrazone, (CH$_2$)$_{11}$ ring | Melting point 157°C monohydrochloride: melting point 186 to 187°C |
| (11) | caprolactam-(4-sulfamoylphenyl)hydrazone · HCl | Melting point 254 to 255°C |
| (12) | caprolactam-(3-methyl-quinolin-2-yl)hydrazone | Melting point 229°C dihydrochloride: decomposition above 245°C |
| (13) | caprolactam-(pyridin-2-yl)hydrazone | Boiling point 175–180°C/0.5 mmHg melting point 133 to 135°C dihydrochloride: melting point 218 to 219°C |
| (14) | caprolactam-(2,4-dinitrophenyl)hydrazone | Melting point 152°C |
| (15) | 3,3,5,5-tetramethyl-pyrrolidinone-(3-chlorophenyl)hydrazone | Boiling point 142–145°C/0.15 mmHg |
| (16) | caprolactam-(2-sulfo-6-chlorophenyl)hydrazone | Melting point 288 to 289°C |

Table 1-continued

| Compound No. | Formula | Physical properties |
|---|---|---|
| (17) | [structure: NH-containing ring with N-NH-phenyl] | Boiling point 170–175°C/0.25 mmHg monohydrochloride: melting point 250 to 255°C (with decomposition) |
| (18) | [structure: (CH₂)₁₁ ring with NH, N-NH-phenyl] | Boiling point 177–180°C/0.08 mmHg monohydrochloride: melting point 228°C |
| (19) | [structure: NH-ring, =N-NH-phenyl-Cl · HCl] | Melting point 260° |
| (20) | [structure: NH-ring, N-NH-phenyl-COOH · HCl] | Decomposes above 220°C |
| (21) | [structure: NH-ring, N-NH-benzimidazolyl] | Melting point 186°C monohydrochloride: melting point 239° to 240°C |
| (22) | [structure: NH-ring, N-NH-benzothiazolyl] | Melting point 147°C to 148°C monohydrochloride: melting point 151 to 153°C |
| (23) | [structure: NH-ring, N-NH-phenyl-CH₃] | Boiling point 165–169°C/0.2 mm Hg monohydrochloride: melting point 246°C (with decomp.) |
| (24) | [structure: NH-ring, N-NH-phenyl-OCH₃] | Boiling point 188–190°C/0.3 mm Hg monohydrochloride: melting point 236–238°C |

Further examples are the following compounds:
4,4-dimethylbutyrolactam-(3-butylmercaptophenyl-hydrazone);
Valerolactam-anthracylhydrazone;
capryllactam-phenanthrylhydrazone;
4-tert.-butylcaprolactam-(3-dimethylaminophenyl-hydrazone).

The fungicidal activity of the compounds which can be prepared according to this invention can be seen from the test example which follows:

EXAMPLE 9

Seed dressing test/stripe disease of barley (seed-borne mycosis)

To produce a suitable dry dressing, the active compound was extended with a mixture of equal parts by weight of talc and kieselguhr to give a finely powdered mixture with the desired concentration of active compound.

To apply the dressing, barley seed, which was naturally infected by *Helminthosporium gramineum*, was shaken with the dressing in a closed glass flask. The seed, on moist filter paper discs in closed Petri dishes, was exposed to a temperature of 4°C for 10 days in a refrigerator. The germination of the barley, and possibly also of the fungus spores, was thereby initiated. Two batches of 50 grains of the pregerminated barley were subsequently sown 2 cm deep in Fruhstorfer standard soil and cultivated in a greenhouse at temperatures of about 18°C in seed boxes which were exposed to light for 16 hours daily. The typical symptoms of the stripe disease developed within 3 to 4 weeks.

After this time, the number of diseased plants was determined as a percentage of the total number of emerged plants. The fewer plants were diseased, the more effective was the active compound.

The active compounds, the concentration of the active compounds in the dressing, the amounts of dressing used and the number of diseased plants can be seen from the following Table:

Table 2

| Active compound | Seed dressing test/stripe disease of barley | | |
|---|---|---|---|
| | Concentration of active compound in the dressing, in % by weight | Amount of dressing used in g/kg of seed | Number of plants with stripe disease, in % of the total emerged plants |
| without dressing | — | — | 30.9 |
| 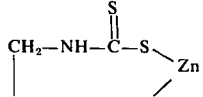 (known) (A) | 10<br>30 | 2<br>2 | 25.6<br>19.0 |
| 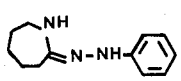 · HCl (3) | 30 | 2 | 1.3 |
| 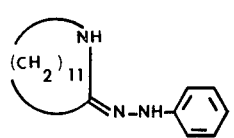 · HCl (18a) | 30 | 2 | 5.2 |
| 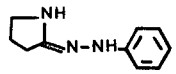 · HCl (17a) | 30 | 2 | 0.0 |
| 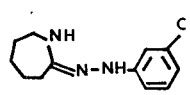 · HCl (1a) | 3<br>10<br>20<br>30 | 2<br>2<br>2<br>2 | 5.3<br>1.4<br>0.0<br>0.0 |
| 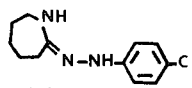 · HCl (2) | 2<br>10<br>30 | 5.1<br>2<br>2 | 1.0<br>0.0 |
| 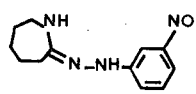 · HCl (4) | 3<br>10<br>30 | 2<br>2<br>2 | 5.1<br>1.0<br>0.0 |
| 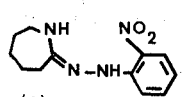 · HCl (6) | 30 | 2 | 1.1 |
| 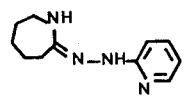 · 2 HCl (13a) | 30 | 2 | 14.6 |
| 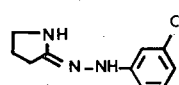 · HCl (19) | 30 | 2 | 1.0 |

Table 2-continued

Seed dressing test/stripe disease of barley

| Active compound | Concentration of active compound in the dressing, in % by weight | Amount of dressing used in g/kg of seed | Number of plants with stripe disease, in % of the total emerged plants |
|---|---|---|---|
| 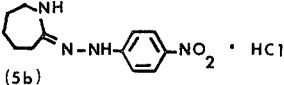 (5b) | 30 | 2 | 0.0 |
| 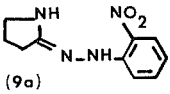 (9a) | 30 | 2 | 3.3 |

It will be appreciated that the instant specification and examples are set forth by way of illustration and not limitation, and that various modifications and changes may be made without departing from the spirit and scope of the present invention.

What is claimed is:

1. In the production of an aryl lactamhydrazone of the formula

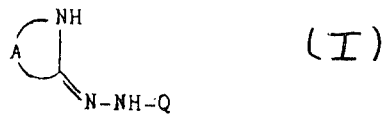 (I)

in which
A represents polymethylene of 3 to 11 carbon atoms, and
Q represents phenyl; phenyl carrying at least one substituent selected from the group consisting of $C_{1-6}$ alkyl, fluorine, chlorine, bromine, nitro and methoxy;

or

substituted by at least one $C_1-C_6$ alkyl, fluorine, chlorine, bromine, methoxy or nitro group,
in which a lactim-ether of the formula

 (II)

in which
R is phenyl or alkyl or 1 to 6 carbon atoms,
is reacted with an arylhydrazine or heteroarylhydrazine of the formula $$H_2N-NH-Q \qquad (III)$$

the improvement which comprises effecting the reaction at a temperature of −20° to 150°C and in the presence of 1 to 10 mole % based on the lactim-ether of an acid catlyst selected from the group consisting of aluminum chloride, iron (III) chloride, boron fluoride, tin (II) chloride, tin (IV) chloride, titanium (V) chloride and antimony pentachloride.

2. The process according to claim 1, in which R is methyl, ethyl or phenyl.

3. The process according to claim 1, in which the reaction is effected between about −10° and +100°C in the presence of a polar solvent and with the reactants (II) and (III) present in substantially equimolar amounts.

* * * * *